(12) United States Patent
Alexander et al.

(10) Patent No.: US 11,376,237 B2
(45) Date of Patent: Jul. 5, 2022

(54) METHODS OF TREATING BACTERIAL INFECTIONS

(71) Applicant: Melinta Subsidiary Corp., Morristown, NJ (US)

(72) Inventors: Elizabeth Alexander, Maplewood, NJ (US); Jeffrey S. Loutit, Los Altos, CA (US); Michael N. Dudley, San Diego, CA (US)

(73) Assignee: MELINTA SUBSIDIARY CORP., Morristown, NJ (US)

( * ) Notice: Subject to any disclaimer, the term of this patent is extended or adjusted under 35 U.S.C. 154(b) by 231 days.

(21) Appl. No.: 16/753,288

(22) PCT Filed: Oct. 1, 2018

(86) PCT No.: PCT/US2018/053772
§ 371 (c)(1),
(2) Date: Apr. 2, 2020

(87) PCT Pub. No.: WO2019/070591
PCT Pub. Date: Apr. 11, 2019

(65) Prior Publication Data
US 2020/0297695 A1    Sep. 24, 2020

Related U.S. Application Data

(60) Provisional application No. 62/657,402, filed on Apr. 13, 2018, provisional application No. 62/567,702, filed on Oct. 3, 2017.

(51) Int. Cl.
| | | |
|---|---|---|
| *A61K 31/407* | (2006.01) | |
| *A61P 31/04* | (2006.01) | |
| *A61K 9/00* | (2006.01) | |
| *A61K 31/69* | (2006.01) | |

(52) U.S. Cl.
CPC .......... *A61K 31/407* (2013.01); *A61K 9/0019* (2013.01); *A61K 31/69* (2013.01); *A61P 31/04* (2018.01)

(58) Field of Classification Search
CPC ........ A61P 31/04; A61K 31/407; A61K 31/69
See application file for complete search history.

(56) References Cited

FOREIGN PATENT DOCUMENTS

| | | | |
|---|---|---|---|
| WO | WO-2013/0184845 A1 | 12/2013 | |
| WO | WO-2016/0172208 A1 | 10/2016 | |
| WO | WO2018/129479 A1 | 7/2018 | |
| WO | WO-2019/070591 A1 | 4/2019 | |

OTHER PUBLICATIONS

McCarthy, M.W. and Walsh, T.J., "Meropenem/vaborbactam fixed combination for the treatment of patients with complicated urinary tract infections," Drugs of Today, vol. 53, No. 10, pp. 521-530 (2017).
No Author, U.S. Food and Drug Administration label for Vabomere™, manufactured by Facta Farmaceutici, S.p.A. and marketed by the Medicines Company, 24 total pages (initial U.S. Approval: 2017).
Hecker, S.J., et al., "Discovery of a Cyclic Boronic Acid ß-Lactamase Inhibitor {RPX7009) with Utility vs Class A Serine Carbapenemases," J. Med. Chem., vol. 58, pp. 3682-3692 (Mar. 17, 2015).
Patriarca, F., et al., "Risk Factors and Outcomes of Infections by Multidrug-Resistant Gram-Negative Bacteria in Patients Undergoing Hematopoietic Stem Cell Transplantation," Biol. Blood Marrow Transplant, vol. 23, pp. 333-339 (2017).
Wang, Q., et al., "Risk factors and clinical outcomes for carbapenem-resistant *Enterobacteriaceae* nosocomial infections," Eur. J. Clin. Microbial. Infect. Dis., vol. 35, pp. 1679-1689 (published online Jul. 11, 2016).
Wunderink, R.G., et al., "Effect and Safety of Meropenem-Vaborbactam versus Best-Available Therapy in Patients with Carbapenem-Resistant Enterobacteriaceae Infections: The Tango II Randomized Clinical Trial," Infect. Dis. Ther., vol. 7, pp. 439-455 (Oct. 2018).
Paterson, D., et al., "Meropenem-Vaborbactam (Vabomere) vs. Best Available Therapy for Carbapenem-Resistant Enterobacteriaceae Infections in Tango II: Outcomes in Immunocompromised Patients," Poster presented at IDWeek2017, San Diego, CA, 1 total page (Oct. 4-8, 2017).
Fingl, E. and Woodbury, D.M., "Section 1, Introduction—Chapter 1, General Principles," The Pharmacological Basis of Therapeutics, Fifth Edition, edited by Goodman, L.S., et al., Macmillan Publishing Co., Inc., New York, NY, pp. 1-46—49 total pages with TOC (1975).
Menzo, S.L., et al., "New Insight on Epidemiology and Management of Bacterial Bloodstream Infection in Patients with Hematological Malignancies" (Review Article), Mediterr. J. Hematol. Infect. Dis., vol. 7, No. 1, e2015044, 12 total pages (Jul. 2015).
Castanheira, M., et al., "Meropenem-Vaborbactam Activity against Enterobacteriaceae Isolates, Including Carbapenem-Resistant and Carbapenemase-Producing Isolates, Collected in United States (US) Hospitals During 2016" (Poster), Presented at ASM Microbe, New Orleans, LA, 1 total page (Jun. 1-5, 2017).
International Search Report and Written Opinion dated Nov. 30, 2018 by Australian Patent Office as International Searching Authority in International Patent Application No. PCT/US2018/053772 (9 total pages).

*Primary Examiner* — Noble E Jarrell
(74) *Attorney, Agent, or Firm* — Wilmer Cutler Pickering Hale and Dorr LLP

(57) ABSTRACT

Methods of treating bacterial infection in immunocompromised subjects and subjects with one or more underlying malignancies include administering a combination of meropenem and vaborbactam to the subject. Suitable subjects to be treated can include a subject with a history of ongoing leukemia or lymphoma, a subject that has had an organ transplant, stem cell transplant, bone marrow transplant, or splenectomy, a subject receiving immunosuppressive medications, a subject receiving bone marrow ablative chemotherapy, a subject with neutropenia and subject suffering from or having suffered from a malignancy.

20 Claims, 2 Drawing Sheets

METHODS OF TREATING BACTERIAL INFECTIONS

This application is a U.S. National Stage application under 35 U.S.C. § 371 of International Patent Application No. PCT/US2018/053772, filed Oct. 1, 2018, which claims the benefit and priority of U.S. Provisional Patent Application Nos. 62/567,702, filed Oct. 3, 2017, and 62/657,402, filed Apr. 13, 2018, each of which is incorporated by reference in its entirety for all purposes.

STATEMENT REGARDING FEDERALLY SPONSORED R&D

This invention was made with federal funds from the Department of Health and Human Services; Office of the Assistant Secretary for Preparedness and Response; Biomedical Advanced Research and Development Authority (BARDA), under Contract No. HHSO100201400002C with Rempex Pharmaceuticals, Inc.

BACKGROUND

Field

The present disclosure relates to antimicrobial compounds, compositions, their use and preparation as therapeutic agents, and methods of treating various bacterial infections.

Description of the Related Technology

Bacterial infections are contagious and may result in many serious or life-threatening complications. Antibiotics have been effective tools in combating bacterial infections for during the last half-century. Some bacterial infections are particularly problematic and resistant to treatment. Gram-negative bacteria cause infections including pneumonia, bloodstream infections, and wound infections. However, many gram-negative bacteria are resistant to multiple antibiotics available on the market and present significant risks to patients, including those who are immunocompromised and/or have other underlying conditions.

Carbapenem-resistant Enterobacteriaceae (CRE) are Gram-negative bacteria that are resistant to the carbapenem class of antibiotics, which are considered the drugs of last resort for such infections. The prognosis of CRE infections ranges from fair to poor; the bacteria can kill up to half of patients who get bloodstream infections.

Immunocompromised subjects are at high risk for mortality from CRE. Up to 33% of all CRE subjects have underlying immune compromise. Among immunocompromised subjects with infections due to CRE pathogens, mortality rates range from 30% to 60%. Additionally, subjects with cancer, including hematological malignancies and solid tumors, are at high risk for mortality due to infections caused by CRE. Among cancer subjects with CRE infections, mortality rates are extremely high in both subjects with solid tumors and hematologic malignancy. Increased risk of mortality due to CRE infection may arise from prolonged hospital stays, frequent use of broad-spectrum antimicrobials, underlying immunocompromise, impaired barrier mechanisms (e.g. mucositis), and impaired host defenses.

Treating gram-negative bacterial infections such as CRE with the current best available treatment may be problematic due to antibiotic resistance. Accordingly, there exists a particular need for methods of treating bacterial infections with antibiotic agents improve patient outcome.

SUMMARY

Some embodiments of the present disclosure relate to methods of treating various bacterial infections, comprising administering a combination of an amount of vaborbactam or a pharmaceutically acceptable salt thereof and an amount of meropenem to a subject in need thereof:

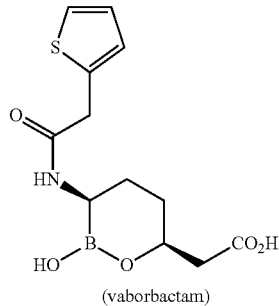 [SMILES: O=C(O)C[C@@H]1CC[C@H](NC(=O)Cc2cccs2)B(O)O1]

(vaborbactam)

In some embodiments, the combination of vaborbactam and meropenem are administered to immunocompromised subjects. In various embodiments, the immunocompromised subjects include subjects suffering from leukemia or lymphoma, subjects taking immunosuppressive medication (for example, taking high-dose systemic steroids), subjects having had a splenectomy, and subjects having neutropenia (e.g., an absolute neutrophil count <1000 cells/mm$^3$). In some embodiments, the immunocompromised subjects have had a tissue transplant (e.g., organ transplant, bone marrow transplant, or stem cell transplant).

In other embodiments, the combination of vaborbactam and meropenem are administered to subjects suffering from or has suffered from one or more underlying malignancies. In various embodiments, the underlying malignancy may be hematological malignancy or a solid tumor. In some embodiments, the hematological malignancy may be selected from acute lymphocytic leukemia, acute myeloid leukemia, AIDS-related lymphoma, primary CNS lymphoma, Burkitt lymphoma, chronic lymphocytic leukemia, chronic myelogenous leukemia, Hodgkin lymphoma, leukemia, multiple myeloma, myeloproliferative neoplasms, and Sezary syndrome.

DETAILED DESCRIPTION OF THE PREFERRED EMBODIMENTS

Definitions

Figure 1:
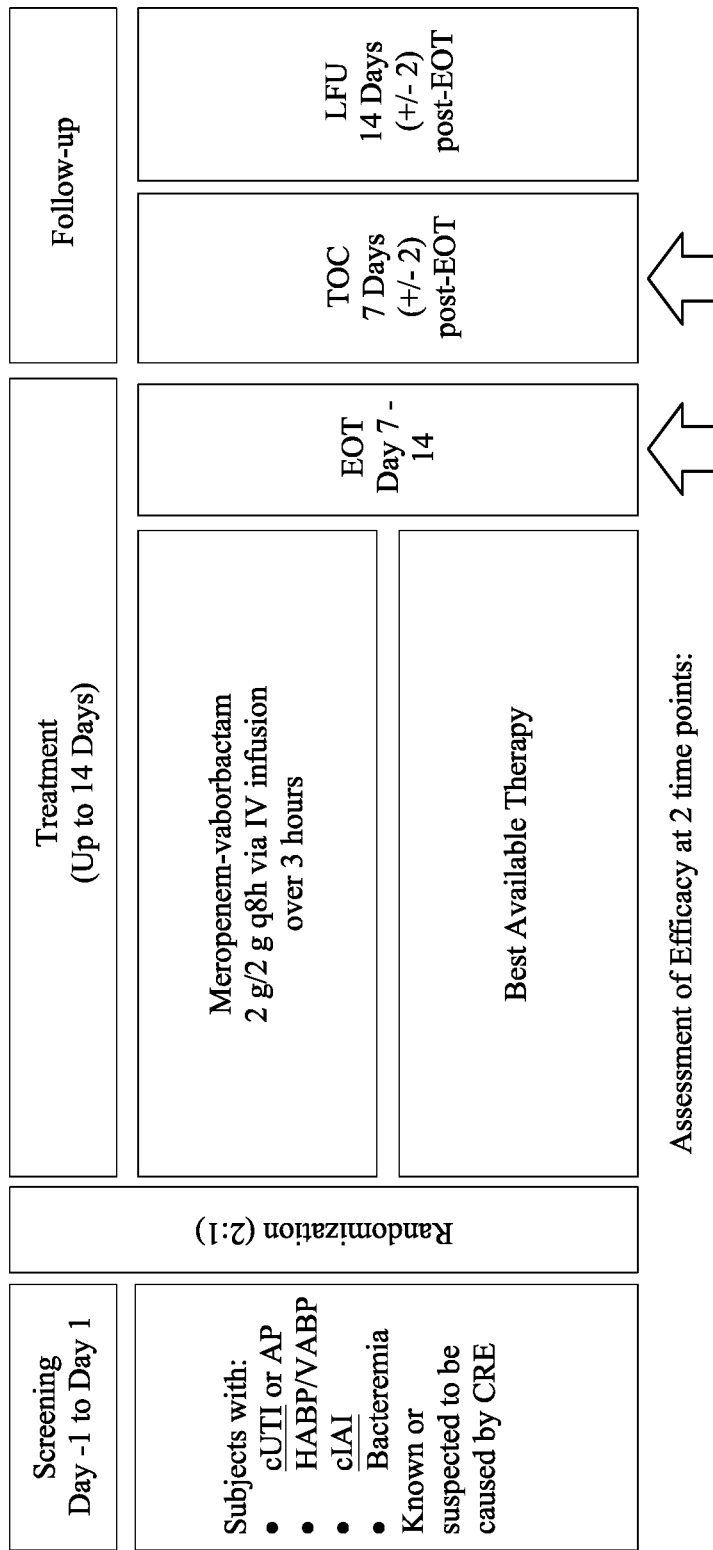
FIG. 1 shows the study schema for studying outcomes among immunocompromised subjects in a randomized, open-label comparative trial with best available therapy (BAT) in subjects with complicated urinary tract infection (cUTI), acute pyelonephritis (AP), hospital-acquired and ventilator-associated bacterial pneumonia (HABP/VABP), bacteremia, and complicated interabdominal infections (cIAI), due to known or suspected carbapenem-resistant Enterobacteriaceae (CRE).

As used herein, a "subject" refers to an animal that is the object of treatment, observation or experiment. "Animal"

includes cold- and warm-blooded vertebrates and invertebrates such as fish, shellfish, reptiles, and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional, such as a Medical Doctor (i.e. Doctor of Allopathic medicine or Doctor of Osteopathic medicine) or a Doctor of Veterinary Medicine, to attempt to cure, or at least ameliorate the effects of, a particular disease or disorder or to prevent the disease or disorder from occurring in the first place.

As used herein, "treat," "treatment," or "treating" refers to administering a pharmaceutical composition for prophylactic and/or therapeutic purposes. The term "prophylactic treatment" refers to treating a patient who does not yet have the relevant disease or disorder, but who is susceptible to, or otherwise at risk of, a particular disease or disorder, whereby the treatment reduces the likelihood that the patient will develop the disease or disorder. The term "therapeutic treatment" refers to administering treatment to a patient already having a disease or disorder.

As used herein, "administration" or "administering" refers to a method of giving a dosage of a pharmaceutically active ingredient to a vertebrate.

As used herein, a "dosage" refers to an amount of therapeutic agent administered to a patient.

As used herein, a "daily dosage" refers to the total amount of therapeutic agent administered to a patient in a day.

As used herein, the term "therapeutic agent" means a substance that is effective in the treatment of a disease or condition.

As used herein, "therapeutically effective amount" or "pharmaceutically effective amount" is meant an amount of therapeutic agent, which has a therapeutic effect. The dosages of a pharmaceutically active ingredient which are useful in treatment are therapeutically effective amounts. Thus, as used herein, a therapeutically effective amount means those amounts of therapeutic agent which produce the desired therapeutic effect as judged by clinical trial results and/or model animal studies.

As used herein, a "therapeutic effect" relieves, to some extent, one or more of the symptoms of a disease or disorder. For example, a therapeutic effect may be observed by a reduction of the subjective discomfort that is communicated by a subject (e.g., reduced discomfort noted in self-administered patient questionnaire).

Treatment of Bacterial Infection

In one aspect, the present disclosure relates to the treatment of a subject that may be suffering from one or more bacterial infections. In some embodiments, the subject may be infected with a gram-negative bacteria. In one embodiment, the subject may be infected with *Escherichia coli*. In one embodiment, the subject may be infected with *Klebsiella pneumoniae*. In one embodiment, the subject may be infected with *Pseudomonas aeruginosa*. In one embodiment, the subject may be infected with *Enterobacter cloacae* species complex. In one embodiment, the subject may be infected with *Enterococcus faecium*. In one embodiment, the subject may be infected with *Serratia marcescens*. In one embodiment, the subject may be infected with *Streptococcus pyogenes*. In one embodiment, the subject may be infected with *Streptococcus pneumoniae*. In one embodiment, the subject may be infected with *Haemophilus influenzae*. In one embodiment, the subject may be infected with *Chlamydia trachomatis*. In one embodiment, the subject may be infected with *Mycoplasma pneumoniae*. In one embodiment, the subject may be infected with *Legionella pneumophila*. In one embodiment, the subject may be infected with *Acinetobacter baumannii*. In one embodiment, the subject may be infected with *Bartonella bacilliformis*. In one embodiment, the subject may be infected with *Brucella* species. In one embodiment, the subject may be infected with *Calymmatobacterium granulomatis*. In one embodiment, the subject may be infected with *Campylobacter fetus*. In one embodiment, the subject may be infected with *Francisella tularensis*. In one embodiment, the subject may be infected with *Haemophilus ducreyi*. In one embodiment, the subject may be infected with *Vibrio cholerae*. In one embodiment, the subject may be infected with *Yersinia pestis*.

In some embodiments, the subject may be immunocompromised. For example, an immunocompromised subject have or more of the following: medical history of ongoing leukemia or lymphoma, history of prior organ transplantation or spleenectomy, ongoing receipt of immunosuppressive medications including high-dose steroids (≥20 mg/kg/day prednisone or equivalent), ongoing receipt of bone marrow ablative chemotherapy, and neutropenia (ANC ≤1000 cells/mm$^3$).

In some embodiments, the subject may have an absolute neutrophil count (ANC) of less than or equal to 1500 cells/mm$^3$. In some embodiments, the subject may have an ANC of less than or equal to 1450 cells/mm$^3$. In some embodiments, the subject may have an ANC of less than or equal to 1400 cells/mm$^3$. In some embodiments, the subject may have an ANC of less than or equal to 1350 cells/mm$^3$. In some embodiments, the subject may have an ANC of less than or equal to 1300 cells/mm$^3$. In some embodiments, the subject may have an ANC of less than or equal to 1250 cells/mm$^3$. In some embodiments, the subject may have an ANC of less than or equal to 1200 cells/mm$^3$. In some embodiments, the subject may have an ANC of less than or equal to 1150 cells/mm$^3$. In some embodiments, the subject may have an ANC of less than or equal to 1100 cells/mm$^3$. In some embodiments, the subject may have an ANC of less than or equal to 1050 cells/mm$^3$. In some embodiments, the subject may have an ANC of less than or equal to 1000 cells/mm$^3$. In some embodiments, the subject may have an ANC of less than or equal to 950 cells/mm$^3$. In some embodiments, the subject may have an ANC of less than or equal to 900 cells/mm$^3$. In some embodiments, the subject may have an ANC of less than or equal to 800 cells/mm$^3$. In some embodiments, the subject may have an ANC of less than or equal to 750 cells/mm$^3$. In some embodiments, the subject may have an ANC of less than or equal to 700 cells/mm$^3$. In some embodiments, the subject may have an ANC of less than or equal to 650 cells/mm$^3$. In some embodiments, the subject may have an ANC of less than or equal to 600 cells/mm$^3$. In some embodiments, the subject may have an ANC of less than or equal to 550 cells/mm$^3$. In some embodiments, the subject may have an ANC of less than or equal to 500 cells/mm$^3$. In some embodiments, the subject may have an ANC of less than or equal to 450 cells/mm$^3$. In some embodiments, the subject may have an ANC of less than or equal to 400 cells/mm$^3$. In some embodiments, the subject may have an ANC of less than or equal to 350 cells/mm$^3$. In some embodiments, the subject may have an ANC of less than or equal to 300 cells/mm$^3$.

In some embodiments, the subject may have an ANC in the range of 300 to 500 cells/mm$^3$. In some embodiments, the subject may have an ANC in the range of 500 to 1000 cells/mm$^3$. In some embodiments, the subject may have an ANC in the range of 1000 to 1500 cells/mm$^3$. In some embodiments, the subject may have an ANC in the range of 500 to 1500 cells/mm$^3$. In some embodiments, the subject may have an ANC in the range of 500 to 750 cells/mm$^3$. In some embodiments, the subject may have an ANC in the range of 750 to 1000 cells/mm$^3$.

In some embodiments, the subject may have or have previously had an underlying malignancy. In some embodiments, the subject may have a hematological malignancy. For example, the patient may have or previously have had a hematological malignancy including but not limited to: acute lymphocytic leukemia, acute myeloid leukemia, AIDS-related lymphoma, primary CNS lymphoma, Burkitt lymphoma, chronic lymphocytic leukemia, chronic myelogenous leukemia, Hodgkin lymphoma, leukemia, multiple myeloma, myeloproliferative neoplasms, and Sezary syndrome. In some embodiments, the subject may have or have had a solid tumor, for example a sarcoma or carcinoma. In some embodiments, the subject may have or have had one or more hematological malignancy or solid tumor.

Pharmaceutical Compositions

In another aspect, the present disclosure relates to a pharmaceutical composition comprising a physiologically acceptable surface active agents, carriers, diluents, excipients, smoothing agents, suspension agents, film forming substances, and coating assistants, or a combination thereof; and a compound disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The meropenem and/or vaborbactam can be formulated for administration with a pharmaceutically acceptable carrier or diluent. The meropenem and/or vaborbactam can be formulated as a medicament with a standard pharmaceutically acceptable carrier(s) and/or excipient(s) as is routine in the pharmaceutical art. The exact nature of the formulation will depend upon several factors including the desired route of administration. Typically, meropenem and/or vaborbactam are formulated for oral, inhalation, intravenous, intragastric, intravascular or intraperitoneal administration.

The term "pharmaceutical composition" refers to a mixture of a compound or compounds disclosed herein with other chemical components, such as diluents or carriers. The pharmaceutical composition facilitates administration of the compound(s) to an organism. Multiple techniques of administering a compound exist in the art including, but not limited to, oral, injection, aerosol, parenteral, and topical administration. Pharmaceutical compositions can also be obtained by reacting compound(s) with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines a chemical compound diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compound or combination of compounds disclosed herein may be found in "Remington's Pharmaceutical Sciences," Mack Publishing Co., Easton, Pa., 18th edition, 1990.

Some embodiments provide the compound(s) or combination of compounds disclosed herein in tablets, film coated tablets, capsules, caplets, pills, gel caps, pellets, beads, or dragée dosage forms. Preferably, the formulations disclosed herein can provide favorable drug processing qualities, including, for example, but not limited to, rapid tablet press speeds, reduced compression force, reduced ejection forces, blend uniformity, content uniformity, uniform dispersal of color, accelerated disintegration time, rapid dissolution, low friability (preferable for downstream processing such as packaging, shipping, pick-and-pack, etc.) and dosage form physical characteristics (e.g., weight, hardness, thickness, friability) with little variation.

The compound(s) or combination of compounds disclosed herein can be formulated readily, for example, by combining the drug substance with any suitable pharmaceutically acceptable excipient(s) for example, but not limited to, binders, diluents, disintegrants, lubricants, fillers, carriers, coatings, glidants, flavours, color additives, and the like, as set forth below. Such compositions can be prepared for storage and for subsequent processing.

Excipients

Acceptable excipients for therapeutic use are well known in the pharmaceutical art, and are described, for example, in Handbook of Pharmaceutical Excipients, 5th edition (Raymond C Rowe, Paul J Sheskey and Sian C Owen, eds. 2005), and Remington: The Science and Practice of Pharmacy, 21st edition (Lippincott Williams & Wilkins, 2005), each of which is hereby incorporated in its entirety. The term "carrier" material or "excipient" herein can mean any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule, tablet, film coated tablet, caplet, gel cap, pill, pellet, bead, and the like suitable for oral administration. Excipients can include, by way of illustration and not limitation, diluents, disintegrants, binding agents, wetting agents, polymers, lubricants, glidants, coatings, sweetens, solubilizing agents, substances added to mask or counteract a disagreeable taste or odor, flavors, colorants, fragrances, and substances added to improve appearance of the composition.

The compositions and formulations can include any other agents that provide improved transfer, delivery, tolerance, and the like. These compositions and formulations can include, for example, powders, pastes, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax.

Any of the foregoing mixtures can be appropriate in treatments and therapies in accordance with the disclosure herein, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol. Pharmacol. 32(2):210-8 (2000), Charman W N "Lipids, lipophilic drugs, and oral drug delivery-some emerging concepts." J. Pharm. Sci. 89(8):967-78 (2000), and the citations therein for additional information related to formulations, excipients and carriers well known to pharmaceutical chemists.

In some embodiments, one or more, or any combination of the listed excipients can be specifically included or excluded from the formulations and/or methods disclosed herein. As will be appreciated by those of skill in the art, the amounts of excipients will be determined by drug dosage and dosage form size.

Lubricants

In some embodiments, lubricants are employed in the manufacture of certain dosage forms. For example, a lubricant will often be employed when producing tablets. In some embodiments, a lubricant can be added just before the tableting step, and can be mixed with the formulation for a minimum period of time to obtain good dispersal. In some embodiments, one or more lubricants can be used. Examples of suitable lubricants include, but are not limited to, magnesium stearate, calcium stearate, zinc stearate, stearic acid, talc, glyceryl behenate, polyethylene glycol, polyethylene oxide polymers (for example, available under the registered trademarks of Carbowax® for polyethylene glycol and Polyox® for polyethylene oxide from Dow Chemical Company, Midland, Mich.), sodium lauryl sulfate, magnesium lauryl sulfate, sodium oleate, sodium stearyl fumarate, DL-leucine, colloidal silica, and others as known in the art. Typical lubricants are magnesium stearate, calcium stearate, zinc stearate and mixtures of magnesium stearate with sodium lauryl sulfate.

Color Additives

In some embodiments, color additives also can be included. The colorants can be used in amounts sufficient to distinguish dosage form strengths. Preferably, color additives approved for use in drugs (21 CFR 74, which is incorporated herein by reference in its entirety) are added to the commercial formulations to differentiate tablet strengths. The use of other pharmaceutically acceptable colorants and combinations thereof are encompassed by the current disclosure.

Binders

Binders can be used, for example, to impart cohesive qualities to a formulation, and thus ensure that the resulting dosage form remains intact after compaction. Suitable binder materials include, but are not limited to, microcrystalline cellulose, gelatin, sugars (including, for example, sucrose, glucose, dextrose and maltodextrin), polyethylene glycol, waxes, natural and synthetic gums, polyvinylpyrrolidone, pregelatinized starch, povidone, cellulosic polymers (including, for example, hydroxypropyl cellulose (HPC), hydroxypropyl methylcellulose (HPMC), methyl cellulose, hydroxyethyl cellulose, and the like), hydroxypropyl cellulose (HPC), and the like. Accordingly, in some embodiments, the formulations disclosed herein can include at least one binder to enhance the compressibility of the major excipient(s). In some embodiments, the binder(s) is(are) sprayed on from solution, e.g. wet granulation, to increase binding activity.

Disintegrants

In some embodiments, disintegrants are used, for example, to facilitate tablet disintegration after administration, and are generally starches, clays, celluloses, algins, gums, or crosslinked polymers. Suitable disintegrants include, but are not limited to, crosslinked polyvinylpyrrolidone (PVP-XL), sodium starch glycolate, alginic acid, methacrylic acid DYB, microcrystalline cellulose, crospovidone, polacriline potassium, sodium starch glycolate, starch, pregelatinized starch, croscarmellose sodium, and the like. If desired, the pharmaceutical formulation can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, sodium lauryl sulfate, dioctyl sodium sulfosuccinate, polyoxyethylene sorbitan fatty acid esters, etc. and the like.

Coatings

In some embodiments, the formulations can include a coating, for example, a film coating. Where film coatings are involved, coating preparations can include, for example, a film-forming polymer, a plasticizer, or the like. Also, the coatings can include pigments and/or opacifiers. Non-limiting examples of film-forming polymers include hydroxypropyl methylcellulose, hydroxypropyl cellulose, methylcellulose, polyvinyl pyrrolidine, and starches. Non-limiting examples of plasticizers include polyethylene glycol, tributyl citrate, dibutyl sebecate, castor oil, and acetylated monoglyceride. Furthermore, non-limiting examples of pigments and opacifiers include iron oxides of various colors, lake dyes of many colors, titanium dioxide, and the like.

Diluents

In some embodiments, diluents are used, and are generally selected from one or more of the compounds sucrose, fructose, glucose, galactose, lactose, maltose, invert sugar, calcium carbonate, lactose, starch, microcrystalline cellulose, lactose monohydrate, calcium hydrogen phosphate, anhydrous calcium hydrogen phosphate, a pharmaceutically acceptable polyol such as xylitol, sorbitol, maltitol, mannitol, isomalt and glycerol, polydextrose, starch, or the like, or any mixture thereof.

Surfactants

In some embodiments, surfactants are used. The use of surfactants as wetting agents in oral drug forms is described in the literature, for example in H. Sucker, P. Fuchs, P. Speiser, Pharmazeutische Technologie, 2nd edition, Thieme 1989, page 260. It is known from other papers, such as published in Advanced Drug Delivery Reviews (1997), 23, pages 163-183, that it is also possible to use surfactants, inter alia, to improve the permeation and bioavailability of pharmaceutical active compounds. Examples of surfactants include, but are not limited to, anionic surfactants, non-ionic surfactants, zwitterionic surfactants and a mixture thereof. Preferably, the surfactants is selected from the group consisting of poly(oxyethylene) sorbitan fatty acid ester, poly(oxyethylene) stearate, poly(oxyethylene) alkyl ether, polyglycolated glyceride, poly(oxyethylene) castor oil, sorbitan fatty acid ester, poloxamer, fatty acid salt, bile salt, alkyl sulfate, lecithin, mixed micelle of bile salt and lecithin, glucose ester vitamin E TPGS (D-α-tocopheryl polyethylene glycol 1000 succinate), sodium lauryl sulfate, and the like, and a mixture thereof.

Glidants

In some embodiments, glidants are used. Examples of glidants which may be used include, but are not limited to, colloidal silicon dioxide, magnesium trisilicate, powdered cellulose, starch, talc and calcium phosphate, or the like, and mixtures thereof.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compound or combination of compounds disclosed herein can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present disclosure may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present disclosure thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compound(s) or combination of compounds disclosed herein can be formulated readily by combining the active compound with pharmaceutically acceptable carriers well known in the art. Such carriers enable the compound or combination of compounds disclosed herein to be formulated as tablets, film coated tablets, pills, dragees, capsules, liquids, gels, get caps, pellets, beads, syrups, slurries, suspensions and the like, for oral ingestion by a patient to be treated. Pharmaceutical preparations for oral use can be obtained by combining the active compound with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. In addition, stabilizers can be added. All formulations for oral administration should be in dosages suitable for such administration. In some embodiments, formulations of the compound(s) or combination of compounds disclosed herein with an acceptable immediate release dissolution profile and a robust, scalable method of manufacture are disclosed.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compound or combination of compounds disclosed herein is conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eyedrops, or in gellan gum (Shedden et al., Clin. Ther., 23(3):440-50 (2001)) or hydrogels (Mayer et al., Ophthalmologica, 210(2):101-3 (1996)); ophthalmic ointments; ophthalmic suspensions, such as microparticulates, drug-containing small polymeric particles that are suspended in a liquid carrier medium (Joshi, A., J. Ocul. Pharmacol., 10(1):29-45 (1994)), lipid-soluble formulations (Alm et al., Prog. Clin. Biol. Res., 312:447-58 (1989)), and microspheres (Mordenti, Toxicol. Sci., 52(1):101-6 (1999)); and ocular inserts. All of the above-mentioned references are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compound(s) or combination of compounds disclosed herein may also be formulated in rectal compositions such as suppositories or retention enemas, e.g., containing conventional suppository bases such as cocoa butter or other glycerides.

In addition to the formulations described previously, the compound or combination of compounds disclosed herein may also be formulated as a depot preparation. Such long acting formulations may be administered by implantation (for example subcutaneously or intramuscularly) or by intramuscular injection. Thus, for example, the compound or combination of compounds disclosed herein may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Methods of Administration

The compound(s) or combination of compounds disclosed herein or pharmaceutical compositions may be administered to the patient by any suitable means. Non-limiting examples of methods of administration include, among others, (a) administration though oral pathways, which includes administration in capsule, tablet, granule, spray, syrup, or other such forms; (b) administration through non-oral pathways such as rectal, vaginal, intraurethral, intraocular, intranasal, or intraauricular, which includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the compound or combination of compounds disclosed herein into contact with living tissue.

Pharmaceutical compositions suitable for administration include compositions where the compound(s) or combination of compounds disclosed herein is contained in an amount effective to achieve its intended purpose. The therapeutically effective amount of the compound or combination of compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, and the specific use for which the compound or combination of compounds disclosed herein are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

As used herein, a "dosage" refers to the amount of the active pharmaceutical ingredients (e.g., meropenem and vaborbactam).

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be between about 0.1 mg/kg and 4000 mg/kg body weight, preferably between about 1 mg/kg and 1000 mg/kg body weight. Alternatively dosages may be based and calculated upon the surface area of the patient, as understood by those of skill in the art.

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on many factors including the subject being treated, the severity of the affliction, the manner of administration, the judgment of the prescribing physician. The compound or combination of compounds disclosed herein may be administered orally or via injection at a dose from 0.1 mg/kg to 4000 mg/kg of the patient's body weight per day. The dose range for adult humans is generally from 100 mg/day to 100 g/day. Tablets or other forms of presentation provided in discrete units may conveniently contain an amount of the compound or combination of compounds disclosed herein which is effective at such dosage or as a multiple of the same, for instance, units containing 100 mg to 50 g (for example, from about 200 mg to 50 g, from about 400 mg to 20 g, from about 800 mg to 10 g, or from about 1 g to 5 g). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

A typical dose of meropenem is from 1 mg to 50 mg per kg of body weight, for example from 10 mg to 40 mg per kg of body weight, depending on a number of factors, including the age and sex of the patient, the precise disorder being treated, and its severity. In some embodiments, a dosage of meropenem can be from about 1 mg to 5000 mg, for example, from 10 mg to 3000 mg, from 100 mg to 2000 mg, from 200 mg to 1500 mg, or from 500 mg to 1000 mg, or within a range defined by any of the aforementioned values. In some embodiments, a dosage of meropenem can be 250 mg, 500 mg, 750 mg, 1000 mg, 1250 mg, 1500 mg, 1750 mg, 2000 mg, 2250 mg, 2500 mg, 2750 mg, 3000 mg, 3250 mg, 3500 mg, 3750 mg, or 4000 mg, or within a range defined by any of the aforementioned values, A typical dose of vaborbactam is 1 mg to 50 mg per kg of body weight, for example from 10 mg to 40 mg per kg of body weight, depending on a number of factors, including the age and sex of the patient, the precise disorder being treated, and its severity. In some embodiments, a dosage of vaborbactam can be from about 1 mg to 5000 mg, for example, from 10 mg to 3000 mg, from 100 mg to 2000 mg, from 200 mg to 1500 mg, or from 500 mg to 1000 mg, or within a range defined by any of the aforementioned values. In some embodiments, a dosage of vaborbactam can be 250 mg, 500 mg, 750 mg, 1000 mg, 1250 mg, 1500 mg, 1750 mg, 2000 mg, 2250 mg, 2500 mg, 2750 mg, 3000 mg, 3250 mg, 3500 mg, 3750 mg, or 4000 mg, or within a range defined by any of the aforementioned values, In some embodiments, the meropenem and vaborbactam can be administered in a weight ratio from 10:1 to 1:10, for example, from 5:1 to 1:5, from 4:1 to 1:4, from 3:1 to 1:3, from 2:1 to 1:2, or about 1:1. A physician will be able to determine the required dosage of meropenem and vaborbactam for any particular subject.

In some embodiments, the dosage of meropenem can be from 250 mg to 4000 mg and the dosage of vaborbactam can be from 250 mg to 4000 mg. In some embodiments, the dosage of meropenem can be from 500 mg to 3000 mg and the dosage of vaborbactam can be from 500 mg to 3000 mg. In some embodiments, the dosage of meropenem can be from 500 mg to 2000 mg and the dosage of vaborbactam can be from 500 mg to 2000 mg. In some embodiments, the dosage of meropenem can be 500 mg and the dosage of vaborbactam can be 500 mg. In some embodiments, the dosage of meropenem can be 1000 mg and the dosage of vaborbactam can be 1000 mg. In some embodiments, the dosage of meropenem can be 1500 mg and the dosage of vaborbactam can be 1500 mg. In some embodiments, the dosage of meropenem can be 2000 mg and the dosage of vaborbactam can be 2000 mg. In some embodiments, the dosage of meropenem can be 2500 mg and the dosage of vaborbactam can be 2500 mg.

In some embodiments, the meropenem and vaborbactam can be administered once, twice, three times, four times, or more per day. In some embodiments, the meropenem and vaborbactam can be administered every 4 hours, every 6 hours, every 8 hours, every 12 hours, or every 24 hours. For example, in some embodiments, a 2000 mg dosage of meropenem and a 2000 mg dosage of vaborbactam can be administered every 8 hours, every 12 hours, or every 24 hours. In some embodiments, a 1500 mg dosage of meropenem and a 1500 mg dosage of vaborbactam can be administered every 8 hours. In some embodiments, a 1000 mg dosage of meropenem and a 1000 mg dosage of vaborbactam can be administered every 8 hours. In some embodiments, a 1000 mg dosage of meropenem and a 1000 mg dosage of vaborbactam can be can be administered every 12 hours. In some embodiments, a 1000 mg dosage of meropenem and a 1000 mg dosage of vaborbactam can be administered every 24 hours. In some embodiments, a 500 mg dosage of meropenem and a 500 mg dosage of vaborbactam can be administered every 8 hours. In some embodiments, a 500 mg dosage of meropenem and a 500 mg dosage of vaborbactam can be administered every 12 hours. In some embodiments, a 500 mg dosage of meropenem and a 500 mg dosage of vaborbactam can be administered every 24 hours.

The exact formulation, route of administration and dosage for the pharmaceutical compositions of the compound or combination of compounds disclosed herein can be chosen by the individual physician in view of the patient's condition. (See, e.g., Fingl et al. 1975, in "The Pharmacological Basis of Therapeutics," which is hereby incorporated herein by reference, with particular reference to Ch. 1). Typically, the dose range of the composition administered to the patient can be from about 0.1 to about 4000 mg/kg of the patient's body weight. The dosage may be a single one or a series of two or more given in the course of one or more days, as is needed by the patient. In instances where human dosages for compounds have been established for at least some condition, the present disclosure will use those same dosages, or dosages that are between about 0.1% and about 5000%, more preferably between about 25% and about 1000% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. In cases of administration of a pharmaceutically acceptable salt, dosages may be calculated as the free base. In some embodiments, a dosage of the composition is administered 1 to 4 times per day. Alternatively the compositions of the compound or combination of compounds disclosed herein may be administered by continuous intravenous infusion, preferably at a dose of each active ingredient up to 100 g per day. As will be understood by those of skill in the art, in certain situations it may be necessary to administer the compound disclosed herein in amounts that exceed, or even far exceed, the above-stated, preferred dosage range in order to effectively and aggressively treat particularly aggressive diseases or infections. In some embodiments, the compound or combination of compounds disclosed herein will be administered for a period of continuous therapy, for example for a week or more, or for months or years.

In some embodiments, the dosing regimen of the compound(s) or combination of compounds disclosed herein is administered for a period of time, which time period can be, for example, from at least about 1 day to at least about 3 days, from at least about 1 day to at least about 1 week, from at least about 1 day to at least about 10 days, from at 1 day to at least about 4 weeks, from at least about 1 week to at least about 2 weeks, from at least about 1 week to at least about 4 weeks, from at least about 4 weeks to at least about 8 weeks, from at least about 4 weeks to at least about 12 weeks, from at least about 4 weeks to at least about 16 weeks, or longer. The dosing regimen of the compound(s) or combination of compounds disclosed herein can be administered three times a day, twice a day, daily, every other day, three times a week, every other week, three times per month, once monthly, substantially continuously or continuously.

In some embodiments described herein, the meropenem and the vaborbactam may be administered to the subject simultaneously. In some embodiments, the meropenem and vaborbactam may be administered to the subject sequentially. In some embodiments, the meropenem is administered to the subject prior to the administration of vaborbactam to the subject. In some embodiments, the meropenem is administered to the subject subsequent to the administration of vaborbactam to the subject.

In some embodiments, the meropenem and the vaborbactam may be administered using the same route of administration. For example, in some embodiments, the meropenem and vaborbactam may both be administered orally. In some embodiments, the meropenem and vaborbactam may both be administered parenterally. In some embodiments, the meropenem and vaborbactam may both be administered intravenously.

In some embodiments, the meropenem and vaborbactam may be administered using different routes of administration.

Some embodiments provide a method to use an effective amount of the combination of meropenem and vaborbactam disclosed herein in the treatment of bacterial infection in a subject comprising administering to the subject a dosage of the combination of meropenem and vaborbactam disclosed herein containing an amount of about 0.1 g to about 100 g of drug per dose of the compound or combination of compounds disclosed herein, orally, three times per month, once monthly, once weekly, once every three days, once every two days, once per day, twice per day, or three times per day substantially continuously or continuously, for the desired duration of treatment.

Some embodiments provide a method to use an effective amount of the combination of meropenem and vaborbactam disclosed herein in the treatment of a bacterial infection in a subject susceptible to acute kidney injury comprising administering to the subject a dosage of the meropenem and vaborbactam containing an amount of from 0.1 mg to about 4000 mg of each of meropenem and vaborbactam per kilogram of body weight per dose of meropenem and vaborbactam, orally, three times per month, once monthly, once weekly, once every three days, once every two days, once per day, twice per day, or three times per day substantially continuously or continuously, for the desired duration of treatment.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. In some embodiments, compositions can be administered using a regimen which maintains plasma levels above the MEC for 10-90% of the time, for example, between 15-30%, 20-45%, 25-50%, 30-55%, 35-60%, 40-65%, 45-70%, 50-75%, 55-80%, 60-90%, 65-75%, 70-80%, 75-85%, 15-90%, 20-90%, 25-90%, 30-90%, 35-90%, 40-90%, 45-90%, 50-90%, 55-90%, 60-90%, 65-90%, 70-90%, 75-90%, or 80-90%. In some embodiments, compositions can be administered using a regimen which maintains plasma levels above the MEC for 20-90% of the time. In some embodiments, compositions can be administered using a regimen which maintains plasma levels above the MEC for 30-90% of the time, between 40-90% and most typically between 50-90%.

In cases of local administration or selective uptake, the effective local concentration of the drug may not be related to plasma concentration.

The amount of composition administered may be dependent on the subject being treated, on the subject's weight, the severity of the affliction, the manner of administration and the judgment of the prescribing physician.

The compound(s) or combination of compounds disclosed herein can be evaluated for efficacy and toxicity using known methods. For example, the toxicology of the compound or combination of compounds disclosed herein may be established by determining in vitro toxicity towards a cell line, such as a mammalian, and preferably human, cell line. The results of such studies are often predictive of toxicity in animals, such as mammals, or more specifically, humans. Alternatively, the toxicity of the compound or combination of compounds disclosed herein in an animal model, such as mice, rats, rabbits, or monkeys, may be determined using known methods. The efficacy of the compound or combination of compounds disclosed herein may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising the compound or combination of compounds disclosed herein formulated in a compatible pharmaceutical carrier may also be prepared, placed in an appropriate container, and labeled for treatment of an indicated condition.

An effective amount of the meropenem and vaborbactam disclosed herein may be determined by one of ordinary skill in the art. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to portal hypertension.

Pharmaceutical compositions comprising the meropenem and vaborbactam disclosed herein capable of treating bacterial infection in an amount effective therefore, and a pharmaceutically acceptable vehicle or diluent are also disclosed. The compositions of the present disclosure may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation or called for by accepted pharmaceutical practice.

The meropenem and vaborbactam dosages disclosed herein may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents.

The meropenem and vaborbactam disclosed herein, for example, may be administered in a form suitable for immediate release or extended release. Immediate release or extended release may be achieved by the use of suitable pharmaceutical compositions comprising meropenem and vaborbactam, or, particularly in the case of extended release, by the use of devices such as subcutaneous implants or osmotic pumps.

The meropenem and vaborbactam disclosed herein may also be administered liposomally. For example, the active substance can be utilized in a composition such as tablet, capsule, solution or suspension meropenem and vaborbactam disclosed herein or in topical form for wound healing (0.01 to 5% by meropenem and vaborbactam disclosed herein, 1 to 5 treatments per day).

The meropenem and vaborbactam disclosed herein may be compounded in a conventional manner with a physiologically acceptable vehicle or carrier, excipient, binder, preservative, stabilizer, flavor, etc., or with a topical carrier.

The meropenem and vaborbactam disclosed herein can also be formulated in compositions such as sterile solutions or suspensions for parenteral administration. The meropenem and vaborbactam disclosed herein may be compounded with a physiologically acceptable vehicle, carrier, excipient, binder, preservative, stabilizer, etc., in a unit dosage form as called for by accepted pharmaceutical practice. The amount of active substance in these compositions or preparations is preferably such that a suitable dosage in the range indicated is obtained.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. Molded tablets, compressed tablets or freeze-dried tablets are exemplary forms which may be used. Exemplary compositions include those formulating the compound or combination of compounds disclosed herein with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene). For example, the compound or combination of compounds disclosed herein may be administered topically to treat peripheral vascular diseases and as such may be formulated as a cream or ointment.

In some embodiments, the composition disclosed herein can comprise at least 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), or 1.2% (w/w) of a preservative. In some embodiments, the topical composition disclosed herein can comprise 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), 1.2% (w/w), 1.5% (w/w), 2% (w/w), 3% (w/w), 4% (w/w), 5% (w/w), 6% (w/w), 7% (w/w), 8% (w/w), 9% (w/w), 10% (w/w), 20% (w/w) or 30% (w/w) of a preservative or a range defined by any two of the preceding values. In some embodiments, the preservative can include one or more components, two or more components or three or more components.

In some embodiments, the composition disclosed herein can comprise at least 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), or 1.2% (w/w) of a preservative including phenoxyethanol, propyl paraben, and methyl paraben. In some embodiments, the topical composition disclosed herein can comprise 0.1% (w/w), 0.2% (w/w), 0.3% (w/w), 0.4% (w/w), 0.5% (w/w), 0.6% (w/w), 0.7% (w/w), 0.8% (w/w), 0.9% (w/w), 1.0% (w/w), 1.1% (w/w), 1.2% (w/w), 1.5% (w/w), 2% (w/w), 3% (w/w), 4% (w/w), 5% (w/w), 6% (w/w), 7% (w/w), 8% (w/w), 9% (w/w), 10% (w/w), 20% (w/w) or 30% (w/w) of a preservative including phenoxyethanol, propyl paraben, and methyl paraben or a range defined by any two of the preceding values.

In some embodiments, the composition may include colorants, deodorants, fragrances, perfumes, anti-foaming agents, lubricants, natural moisturizing agents, skin conditioning agents, skin protectants, skin benefit agents, solvents, solubilizing agents, suspending agents, wetting agents, humectants, propellants, dyes, pigments, and combinations thereof.

In some embodiments, the composition may include additional components added to enhance the odor, texture or color of the composition. For example, fragrances may be added to enhance odor. For example, emulsifiers or inert spheres may be added to enhance texture. For example, colorants may be added to enhance color.

In some embodiments, the composition may be applied to a body portion, such as a hand, foot, knee, elbow, and the like to treat pain and/or inflammation of the body portion. The composition may be applied by any suitable means, such as rubbing, spraying, rolling, wiping, and the like, and massaged into the body portion to be treated.

In some embodiments, the meropenem and vaborbactam as disclosed and described herein and/or topical compositions thereof can be used in combination therapy with at least one other agent. In some embodiments, the meropenem and vaborbactam disclosed herein and/or topical composition thereof is administered concurrently with the administration of another agent, which may be part of the same topical composition as the compound of the present invention or a different composition. In other embodiments, a topical composition of the present invention is administered prior or subsequent to administration of another agent.

In some embodiments the compositions described herein are incorporated into a patch or film for transdermal drug delivery. In some embodiments, such patches further comprise a porous or resorbable film, an active pharmaceutical agent, and optionally a transdermal carrier or penetration enhancer. Exemplary transdermal carriers include dimethylsulfoxide; 1-dodecylazacycloheptan-2-one or laurocapran; dimethylacetamide; dimethylformamide; lauric acid; myristic acid; capric acid; caprylic acid; oleic acid; diethylene glycol; tetraethylene glycol; terpenes; essential oils of *eucalyptus, chenopodium* and ylang-ylang; dimethyl isosorbide; Oxazolidinones such as 4-decyloxazolidin-2-one; 2-pyrrolidone; N-methyl-2-pyrrolidone; urea; EDTA; Sodium Glycolate; polysorbates; sodium deoxycholate; polyethylene glycol; PLA/PLGA nanoparticles; polymer nanoparticles; block-copolymer nanoparticles, especially those comprising Pluronic®-type polyethylene oxide-block-polypropylene oxide copolymers; porous silica nanoparticles; metallic nanoparticles, especially those comprising gold, palladium, and iron; metal oxide nanoparticles, especially those comprising $TiO_2$ and $Al_2O_3$; short chain alcohols such as ethanol, propanol, and butanol; and oils such as mineral oil and coconut oil. In some embodiments the compositions described herein are incorporated into an adhesive for a transdermal patch. In some further embodiments, the compositions described herein are incorporated into a resorbable film. In some embodiments, the active pharmaceutical agent is contained within a separate reservoir layer. In some embodiments, the transdermal patch consists of a single layer. In some embodiments, the transdermal patch is constructed in multiple layers.

Kits

Some embodiments of the present invention include kits comprising meropenem, vaborbactam or combination thereof. Some kits include a single use container comprising meropenem, vaborbactam or combination thereof. Single use containers include ampules, vials, and the like. The single-use container can comprise a lyophilized formulation of meropenem, vaborbactam or combination thereof. Some kits include a diluent for reconstituting the lyophilized formulations of meropenem, vaborbactam or combination thereof.

In some embodiments, meropenem, vaborbactam, or combination thereof may be prepared for single-dosage use. In this embodiment, the solutions of the invention are lyophilized in individual vials such as 20-mL vials. Upon lyophilization, the vials are stoppered with any acceptable stopper. The stoppered vials are then shipped for use. When needed, the vials can be reconstituted by adding sufficient diluents to achieve the desired concentration of meropenem and/or vaborbactam. The concentration of reconstituted solutions may be easily determined by those of ordinary skill in the art. Any pharmaceutically acceptable diluent may be used. Examples of such diluents include but are not limited to water, 0.9% saline, Lactated Ringer's injection solution and dextrose solutions including 5% dextrose (5DW).

In some embodiments, the diluent does not comprise a pharmaceutically acceptable oil (e.g., polyoxyethylene hydrogenated castor oils), a pyridine-containing compound (e.g., nicotinamide), gluconate, an antioxidant, an alcohol (e.g., a polyhydric alcohol, such as, propylene glycol, ethylene glycol), glycerol, polyethylene glycol, a pyrrolidone-containing compound, a water-miscible local anaesthetic (e.g., procaine, tetracaine), urea, lactose, or a dehydrating agent (e.g., ethyl acetate, acetic anhydride, absolute ethanol, ethyl acetate, acetic anhydride, and mixtures thereof). In some embodiments, the diluent does not comprise a tetracycline-solubilizing cosolvent.

In some embodiments, the diluent contains the divalent or trivalent cation. For example, some embodiments include kits that comprise a first container comprising a diluent that comprises an aqueous solution of a divalent or trivalent cation; and a second container comprising a solid composition soluble in the diluent, wherein the solid composition comprises meropenem in an amount such that the molar ratio of the divalent or trivalent cation to meropenem is greater than about 2:1. In some embodiments, the diluent comprises an acid, e.g., HCl. In some embodiments, the diluent comprises a buffer. In some embodiments, the buffer is sodium acetate.

More embodiments include kits comprising a first container comprising a diluent that comprises an aqueous solution of a divalent or trivalent cation; and a second container comprising a solid composition soluble in the diluent, wherein the solid composition comprises a meropenem, vaborbactam, or a combination thereof in an amount such that the molar ratio of the divalent or trivalent cation to tetracycline antibiotic is greater than 3:1.

More embodiments include single use vials comprising any composition wherein the vial comprises an amount of meropenem, vaborbactam or combination thereof of at least 100 µg, 200 µg, 300 µg, 400 µg, 500 µg, 600 µg, 700 µg, 800 µg, 900 µg, 1000 µg. In some embodiments, the vial comprises an amount of meropenem, vaborbactam or combination thereof of at least 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, and 130 mg. In some embodiments, the vial comprises an amount of meropenem, vaborbactam or combination thereof of at least 100 mg, 200 mg, 300 mg, 400 mg, and 500 mg. In some embodiments, the vial comprises about 1000 mg of meropenem, vaborbactam or combination thereof.

EXAMPLES

Embodiments of the present application are disclosed in further detail in the following examples, which are not in any way intended to limit the scope of the present disclosure.

Example 1

This example describes outcomes among immunocompromised subjects in a randomized, open-label comparative trial with best available therapy (BAT) in subjects with complicated urinary tract infection (cUTI), acute pyelonephritis (AP), hospital-acquired and ventilator-associated bacterial pneumonia (HABP/VABP), bacteremia, and complicated interabdominal infections (cIAI) due to known or suspected CRE. Unlike other trials of new antimicrobials, the trial described herein included subjects with underlying and active malignancy including immunocompromised subjects, subjects with hematologic malignancies, and bone marrow transplant recipients.

The current "best available therapy" for CRE infections involves treatment with one or more of a limited pool of antimicrobials, which have been associated with high levels of toxicity and potential for interaction with immunosuppressive medications. Meropenem-vaborbactam (M-V) is a novel cyclic boronic acid beta-lactamase inhibitor combination being developed for treatment of serious gram-negative infections, including CRE.

Eligible subjects were randomized 2:1 to M-V (2 g/2 g every 8 h) or BAT for 7 to 14 days (FIG. 1). BAT included any of the following, alone or in combination: carbapenems, aminoglycosides, polymyxin B, vaborbactam, tigecycline, or ceftazidime-avibactam (monotherapy only). Clinical cure was defined as a complete resolution of signs/symptoms such that no further antimicrobial therapy was required and was assessed by the blinded investigator (BI) and primary investigator (PI) at two time points: end of treatment (EOT) and test of cure (TOC). In cases where the assessment by the BI and PI differed, clinical cure was adjudicated by the blinded adjudication committee. Microbiologic cure was defined as a composite of microbial eradication or presumed eradication at respective visit.

Key inclusion criteria: known or suspected (evidence of CRE in culture or molecular testing within past 90 d) CRE pathogen, requirement of ≥7 days IV therapy, confirmed cUTI/AP, HABP/VABP, bacteremia, or cIAI. Key exclusion criteria: receipt of >24 hours of potentially effective antimicrobials (unless clinical failure), immediate life-threatening disease, known infection due to NDM, VIM, IMI or OXA-encoded beta-lactamase. Efforts to reduce bias included blinded investigator, blinded adjudication committee, and a source control adjudication committee (for cIAI). Immunocompromised was defined a priori as any subject with one or more of the following: medical history of active leukemia/lymphoma, history of prior organ transplant or splenectomy, active receipt of immunosuppressive medications including high-dose steroids (>20 mg/kg/day for >2 weeks of prednisone or equivalent), active receipt of bone marrow ablative chemotherapy, and/or neutropenia during the study with an absolute neutrophil count <1000 cells/mm$^3$.

Of the 50 subjects who had a baseline pathogen (m-MITT population), 19 (38.0%) were immunocompromised (4 leukemia/lymphoma (21%), 5 medication 26.3%), 10 transplant (52.6%, 7 solid organ transplants, 3 bone marrow/stem cell transplants). Among the 43 subjects with a baseline CRE pathogen (mCRE-MITT), 18 (41.9%) were immunocompromised. Baseline characteristics and baseline pathogens of immunocompromised subjects are shown in Table 1. The most common infection types among immunocompromised subjects (mCRE-MITT) were bacteremia (61.1%), cUTI/AP (16.7%), HABP/VABP (11.1%), and cIAI (11.1%).

TABLE 1

Baseline Characteristics of Immunocompromised Subjects (mCRE-MITT)

|  | M-V N = 10 n, (%) | BAT N = 8 n, (%) |
|---|---|---|
| Immunocompromising condition | | |
| Leukemia/lymphoma | 2 (20.0) | 2 (25.0) |
| medication | 4 (40.0) | 1 (12.5) |
| Steroids[1] | 3 (30.0) | 1 (12.5) |
| Other[2] | 1 (10.0) | 0 (0.0) |
| transplant | 4 (40.0) | 5 (62.5) |
| Solid Organ | 2 (20.0) | 5 (62.5) |
| Bone marrow/stem cell transplant[3] | 2 (20.0) | 0 (0.0) |
| Microbiology of baseline pathogens[4] | | |
| *Klebsiella pneumoniae* | 8 (80.0) | 7 (87.5) |
| *Enterobacter cloacae* species complex | 1 (10.0) | 0 (0.0) |
| *Enterococcus faecium* | 0 (0.0) | 1 (12.5) |
| *Escherichia coli* | 1 (10.0) | 0 (0.0) |
| *Serratia marcescens* | 0 (0.0) | 1 (12.5) |

[1] >20 mg/kg/d prednisone or equivalent.
[2] Anti-rejection medications, bone marrow suppressive chemotherapy.
[3] One bone marrow transplant and one peripheral stem cell transplant.
[4] Baseline pathogens are identified based on both local and central labs. Subjects may have had more than one baseline pathogen.

Figure 2:
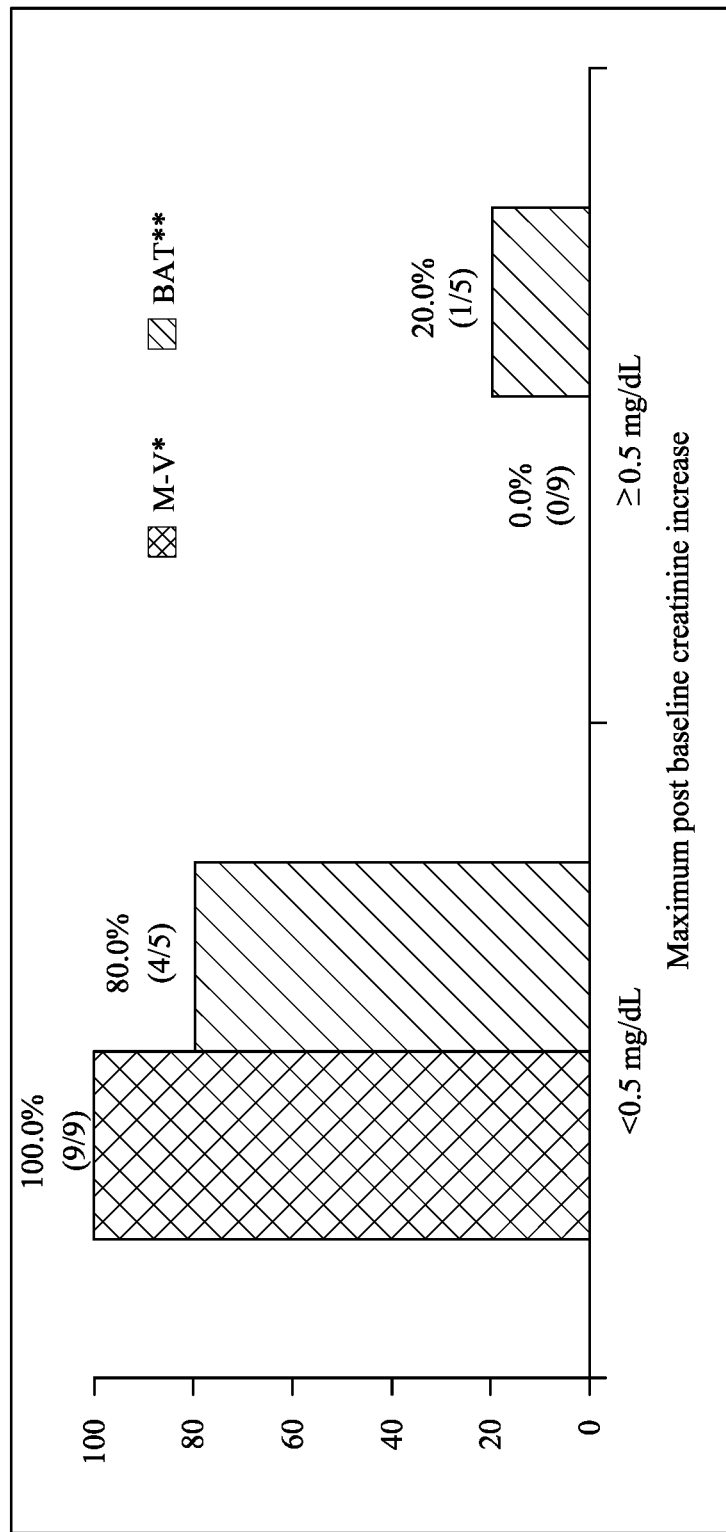
FIG. 2 shows the maximum post-baseline creatinine increase in immunocompromised subjects participating in the study.

Clinical cure rates for mCRE-MITT immunocompromised subjects at EOT and TOC (EOT+7 days) were higher for those in the M-V arm compared to the BAT arm (absolute increase 47.5%, EOT and 70%, TOC) (Table 2). At TOC, the increase in cure rates among immunocompromised subjects receiving M-V vs. BAT achieved statistical significance (95% CI 41.6-98.4, P<0.0001) on ad hoc analysis. Rates of microbial cure (defined as either microbial eradication or presumed eradication) for mCRE-MITT immunocompromised subjects were higher for those in the M-V arm vs. BAT arm (absolute increase of 47.5% at EOT and TOC). The all-cause mortality at Day 28 was lower for those in the M-V arm vs. BAT arm (20% vs. 37.5%) for mCRE-MITT. This was associated with an absolute risk reduction (mortality) of 17.5% and relative risk reduction of 46.7%. The maximum post baseline creatinine increase of <0.5 mg/dL and ≥0.5 mg/dL are shown in FIG. 2.

TABLE 2

Clinical and Microbial Cure Rates and All-Cause Mortality in Immunocompromised Subjects (mCRE-MITT)

|  | M-V N = 10 n, (%) | BAT N = 8 n, (%) | Absolute Difference (M-V − BAT) (95% CI)* | Relative Difference [(M-V − BAT)/BAT] |
|---|---|---|---|---|
| Clinical Cure, EOT | 6 (60) | 1 (12.5) | 47.5% (9.5-85.5; P = .01) | 380% |
| Clinical Cure, TOC (EOT + 7 days) | 7 (70) | 0 (0) | 70% (41.6-98.4; P < .0001) | NA[†] |
| Microbial Cure[‡], EOT | 6 (60) | 1 (12.5) | 47.5 | 380% |
| Microbial Cure[‡], TOC (EOT + 7 days) | 6 (60) | 0 (0.0) | 47.5 | 380% |
| Day 28 All-Cause Mortality | 2 (20) | 3 (37.5) | −17.5% (−59.2%-24.2%; P = .41) | −46.7% |

CI, confidence interval.
Bold font denotes values for which the 95% CI does not cross zero; therefore, statistical significance has been achieved.
*Difference estimates, 95% CI and P values were obtained by Wald test of equality.
[†]Approaches infinity as denominator is zero.
[‡]Composite of microbial eradication or presumed eradication at respective visit.

Among immunocompromised subjects, when compared to BAT, M-V was associated with fewer adverse events (AEs; 84.6% vs. 100%), drug-related AEs (30.8% vs. 40.0%), serious AEs (38.5% vs. 50.0%), discontinuations of study drug or study due to AEs (15.4% vs. 30.0%) and renal-related AEs (7.7% vs. 40.0%) (Table 3).

TABLE 3

Adverse Events and Safety Endpoints in Immunocompromised Subjects (Safety Population)

| Adverse Events | M-V N = 13 n, (%) | BAT N = 8 n, (%) | Total N = 23 n, (%) |
|---|---|---|---|
| TEAEs, n (%) | | | |
| any | 11 (84.6) | 10 (100) | 21 (91.3) |
| Drug-related | 4 (30.8) | 4 (40.0) | 8 (34.8) |
| SAEs, n (%) | | | |
| all | 5 (38.5) | 5 (50.0) | 10 (43.5) |
| Drug-related | 0 (0.0) | 1 (10.0) | 1 (4.3) |
| Study drug discontinuations due to TEAEs, n (%) | 2 (15.4) | 3 (30.0) | 5 (21.7) |
| Study discontinuations due to TEAEs, n (%) | 2 (15.4) | 3 (30.0) | 5 (21.7) |

TABLE 3-continued

Adverse Events and Safety Endpoints in Immunocompromised Subjects (Safety Population)

| Adverse Events | M-V<br>N = 13<br>n, (%) | BAT<br>N = 8<br>n, (%) | Total<br>N = 23<br>n, (%) |
|---|---|---|---|
| Renal-related safety endpoints | | | |
| Renal-related TRAEs (Preferred Term) | 1 (7.7) | 1 (10.0) | 5 (21.7) |
| Anuria | 1 (7.7) | 0 (0.0) | 1 (4.3) |
| Renal failure acute | 0 (0.0) | 2 (20.0) | 2 (8.7) |
| Renal impairment | 0 (0.0) | 2 (20.0) | 2 (8.7) |

SAE, serious adverse event; TEAE, treatment-emergent adverse event; TRAE, treatment-related adverse event.

Treatment of immunocompromised CRE subjects with M-V was associated with higher clinical cure rate (M-V 60% vs. BAT 12.5%, P=0.01) and lower mortality (M-V 20% vs. BAT 37%). Treatment with M-V in immunocompromised subjects was safer than BAT as demonstrated by decreased AEs, including SAEs and renal-related AEs. Adverse event rates are comparable to those seen in the overall M-V population.

Example 2

In this example, an analysis was conducted on the effects of M-V treatment on subjects having an underlying malignancy. The trial was performed according to the methods described in Example 1

Subjects with underlying malignancy included all subjects with the key terms "cancer" or "malignancy" reported in their medical history in the trial. A manual review of all subjects and the qualifying key terms was then performed to ensure validity, in which one subject with a key term of "malignant melanoma removal" was removed from the population. Malignancy was determined by the primary investigator to be either ongoing or not ongoing.

The term "underlying immunocompromised" was defined a priori as any subject with one or more of the following: medical history of ongoing leukemia or lymphoma, history of prior organ transplantation or spleenectomy, ongoing receipt of immunosuppressive medications including high-dose steroids (≥20 mg/kg/day prednisone or equivalent), ongoing receipt of bone marrow ablative chemotherapy, and or neutropenia during the study (ANC≤1000 cells/mm$^3$).

Difference estimates, 95% confidence intervals and P values provided herein were obtained by Wald test of equality.

The trial was conducted as described in Example 1 and FIG. 1. Eligible subjects were randomized 2:1 to M-V (2 g/2 g every 8 h) or BAT for 7 to 14 days. BAT included any of the following, alone or in combination: carbapenems, aminoglycosides, polymyxin B, vaborbactam, tigecycline, or ceftazidime-avibactam (monotherapy only). Clinical cure was defined as a complete resolution of signs/symptoms such that no further antimicrobial therapy was required and was assessed by the blinded investigator (BI) and primary investigator (PI) at two time points: end of treatment (EOT) and test of cure (TOC). In cases where the assessment by the BI and PI differed, clinical cure was adjudicated by the blinded adjudication committee. Microbiologic cure is defined as a composite of microbial eradication or presumed eradication at respective visit.

Key inclusion criteria: known or suspected (evidence of CRE in culture or molecular testing within past 90 d) CRE pathogen, requirement of ≥7 days IV therapy, confirmed cUTI/AP, HABP/VABP, bacteremia, or cIAI. Key exclusion criteria: receipt of >24 hours of potentially effective antimicrobials (unless clinical failure), immediate life-threatening disease, known infection due to NDM, VIM, IMI or OXA-encoded beta-lactamase. Efforts to reduce bias included blinded investigator, blinded adjudication committee, and a source control adjudication committee (for cIAI).

Seventy-two subjects were randomized, 50 (69.4%) of which had a baseline pathogen. Twenty-two (44.0%) had a prior diagnosis of malignancy (14 active diagnoses, 8 inactive-past diagnoses), and 15 of these subjects presented with a CRE pathogen (mCRE-MITT) and with infection types of: bacteremia (53.3%), cUTI/AP (20%), HABP/VABP (13.3%), and cIAI (13.3%). Ten (66.7%) of the subjects in the mCRE-MITT group were also immunocompromised. The baseline characteristics of subjects with cancer in the study are summarized in Table 4.

TABLE 4

Baseline Characteristics of Study Subjects with Cancer (mCRE-MITT population).

| | M-V (n = 8) | BAT (n = 7) |
|---|---|---|
| Underlying Malignancy[1] | | |
| Leukemia/Lymphoma[1] | 4/8 (50.0%) | 2/7 (28.6%) |
| Any Solid Tumor[1] | 4/8 (50.0%) | 5/7 (71.4%) |
| Metastatic Solid Tumor[1] | 2/8 (25.0%) | 2/7 (28.6%) |
| Non-metastatic Solid Tumor[1] | 2/8 (25.0%) | 3/7 (42.9%) |
| Immunocompromised | 6/8 (50.0%) | 4/7 (57.1%) |
| Infection Type | | |
| cUTI/AP | 2/8 (25.0%) | 1/7 (14.3%) |
| cIAI | 0/8 (0) | 2/7 (28.6%) |
| HABP/VABP | 2/8 (25.0%) | 0/7 (0) |
| Bacteremia | 4/8 (50.0%) | 4/7 (57.1%) |

[1]Subjects may have more than one malignancy reported.

A statistically significant increase in clinical cure rate at EOT and TOC was observed in cancer subjects treated with meropenem-vaborbactam compared to those treated with best available therapy (mCRE-MITT population). The absolute increase in clinical cure rate at EOT was 73.2% and at TOC was 75.5% subjects treated with meropenem-vaborbactam. A statistically significant increase in microbiologic cure rate was observed in meropenem-vaborbactam treated cancer subjects (mCRE-MITT population). Receipt of meropenem-vaborbactam was associated with a significant decrease in all-cause mortality at Day 28. The results are summarized below in Table 5.

TABLE 5

Efficacy Outcomes

| Outcomes in Oncology mCRE-MITT | M-V (n = 8) | BAT (n = 7) | All (n = 15) | Absolute Difference (95% CI)[1] |
|---|---|---|---|---|
| Clinical Cure at End of Therapy (EOT) | 7 (87.5%) | 1 (14.3%) | 8 (53.3%) | +73.2%<br>(21.0% to 96.4%) |

TABLE 5-continued

Efficacy Outcomes

| Outcomes in Oncology mCRE-MITT | M-V (n = 8) | BAT (n = 7) | All (n = 15) | Absolute Difference (95% CI)[1] |
|---|---|---|---|---|
| Clinical Cure at Test of Cure (EOT + 7 days) | 6 (75.0%) | 0 (0%) | 6 (40.0%) | +75.5% (27.1% to 96.8%) |
| Microbiologic Cure at Test of Cure (EOT + 7 days)[2] | 5 (62.5%) | 0 (0%) | 5 (33.3%) | +62.5% (14.2% to 92.5%) |
| All Cause Mortality at Day 28 | 1 (12.5%) | 4 (57.1%) | 5 (33.3%) | −44.6% (−82.2% to −10.2%) |

[1]Exact test
[2]Microbioloeic Cure is a composite of microbioloeic eradication and presumed eradication at TOC Clinical cure, microbiologic cure, and mortality amongst the oncology subjects in the mCRE-MITT population are shown in Table 6. M-V was associated with fewer drug-related adverse events (16.7% vs. 33.3%), serious adverse events (25.0% vs. 77.8%), and renal adverse events (8.3% vs. 22.2%) than BAT.

TABLE 6

Adverse Events and Safety Endpoints in Immunocompromised Subjects (Safety Population)

| Adverse Events | M-V (n = 8) | BAT (n = 7) | Total (n = 15) |
|---|---|---|---|
| TEAE, n, (%) | | | |
| Any | 9 (75.0%) | 9 (100.0%) | 18 (85.7%) |
| Drug-Related | 2 (16.7%) | 3 (33.3%) | 5 (23.8%) |
| SAEs, n (%) | | | |
| Any | 3 (25.0%) | 7 (77.8%) | 10 (47.6%) |
| Drug-Related | 0 (0) | 0 (0) | 0 (0) |
| Study Drug Discontinuation due to TEAEs, n (%) | 1 (8.3%) | 2 (22.2%) | 3 (14.3%) |
| Study Discontinuation due to TEAEs, n (%) | 1 (8.3%) | 4 (44.4%) | 5 (23.8%) |
| Renal-related Safety Endpoints | 1 (8.3%) | 2 (22.2%) | 3 (14.3%) |
| Hematuria | 1 (8.3%) | 0 (0) | 1 (4.8%) |
| Renal Failure | 0 (0) | 1 (11.1%) | 1 (4.8%) |
| Renal Failure Acute | 1 (8.3%) | 1 (11.1%) | 2 (9.5%) |

Approximately one-third of subjects in this trial with a qualifying baseline CRE pathogen (mCRE-MITT population) had a prior or ongoing malignancy. Subjects with underlying malignancies (both solid tumor and leukemia/lymphoma) are at increased risk for both infection and mortality due to CRE pathogens. Treatment of cancer subjects, including immunocompromised cancer subjects, with meropenem-vaborbactam was associated with a significantly higher clinical and microbiologic cure rate compared to BAT. Treatment of cancer subjects, including immunocompromised cancer subjects, with meropenem-vaborbactam was associated with a 44.6% absolute risk reduction in Day 28 mortality. Treatment with meropenem-vaborbactam was associated with decreased adverse events, including serious adverse events and renal-related adverse events, than BAT among cancer subjects. The results of the trial indicate that meropenem-vaborbactam is a promising new treatment option for CRE infections in this vulnerable patient population.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method of treating one or more bacterial infection in a subject, wherein the subject is immunocompromised, comprising administering to the subject in need thereof a combination of meropenem and vaborbactam.

2. The method of claim 1, wherein the bacterial infection is selected from the group consisting of *Escherichia coli*, *Klebsiella pneumoniae*, *Pseudomonas aeruginosa*, *Enterobacter cloacae* species complex, *Enterococcus faecium*, *Serratia marcescens*, *Streptococcus pyogenes*, *Streptococcus pneumoniae*, *Haemophilus influenzae*, *Chlamydia trachomatis*, *Mycoplasma pneumoniae*, and *Legionella pneumophila*, *Acinetobacter baumannii*, *Bartonella bacilliformis*, *Brucella* species, *Calymmatobacterium granulomatis*, *Campylobacter fetus*, *Francisella tularensis*, *Haemophilus ducreyi*, *Vibrio cholerae*, and *Yersinia pestis*.

3. The method of claim 1, wherein the subject has a history of ongoing leukemia or lymphoma.

4. The method of claim 1, wherein the subject has had an organ transplant, stem cell transplant, bone marrow transplant, or splenectomy.

5. The method of claim 1, wherein the subject is receiving immunosuppressive medications.

6. The method of claim 1, wherein the subject is receiving bone marrow ablative chemotherapy.

7. The method of claim 1, wherein the subject has neutropenia.

8. The method of claim 1, wherein the subject is suffering from or has suffered from a malignancy.

9. A method of treating one or more bacterial infection in a subject, wherein the subject is suffering from or has suffered from a malignancy, comprising administering to the subject in need thereof a combination of meropenem and vaborbactam.

10. The method of claim 9, wherein the bacterial infection is selected from the group consisting of *Escherichia coli*, *Klebsiella pneumoniae*, *Pseudomonas aeruginosa*, *Enterobacter cloacae* species complex, *Enterococcus faecium*, *Serratia marcescens*, *Streptococcus pyogenes*, *Streptococcus pneumoniae*, *Haemophilus influenzae*, *Chlamydia trachomatis*, *Mycoplasma pneumoniae*, and *Legionella pneumophila*, *Acinetobacter baumannii*, *Bartonella bacilliformis*, *Brucella* species, *Calymmatobacterium granulomatis*, *Campylobacter fetus*, *Francisella tularensis*, *Haemophilus ducreyi*, *Vibrio cholerae*, and *Yersinia pestis*.

11. The method of claim 8, wherein the malignancy is a hematological malignancy, and wherein the hematological malignancy is selected from the group consisting of acute lymphocytic leukemia, acute myeloid leukemia, AIDS-related lymphoma, primary CNS lymphoma, Burkitt lymphoma, chronic lymphocytic leukemia, chronic myelogenous leukemia, Hodgkin lymphoma, leukemia, multiple myeloma, myoproliferative neoplasms, and Sezary syndrome.

12. The method of claim 8, wherein the subject is suffering from or has suffered from a solid tumor, and wherein the solid tumor is a sarcoma or carcinoma.

13. The method of claim 1, wherein the subject has an absolute neutrophil count below about 1000 cells/mm$^3$.

14. The method of claim 1, wherein the administration is oral, intravenous, intraperitoneal, intragastric, or intravascular administration.

15. The method of claim 1, wherein the dose of the meropenem administered is between 1 mg and 5000 mg and the dose of the vaborbactam administered is between 1 mg and 5000 mg.

16. The method of claim 15, wherein the dose of meropenem is 10 mg to 3000 mg and the dose of vaborbactam is 10 mg to 3000 mg.

17. The method of claim 15, wherein the dose of meropenem is 100 mg to 2000 mg and the dose of vaborbactam is 100 mg to 2000 mg.

18. The method of claim 1, wherein the meropenem and vaborbactam are administered in a weight ratio from 2:1 to 1:2.

19. The method of claim 1, wherein the meropenem and the vaborbactam are administered from one to four times daily, and wherein the meropenem and vaborbactam are administered from about 1 day to at least about 4 weeks.

20. The method of claim 1, wherein the meropenem and vaborbactam are administered simultaneously.

* * * * *